(12) United States Patent
Manack et al.

(10) Patent No.: US 8,470,337 B2
(45) Date of Patent: Jun. 25, 2013

(54) THERAPEUTIC TREATMENTS USING BOTULINUM NEUROTOXIN

(75) Inventors: Aubrey N. Manack, Costa Mesa, CA (US); Mitchell F. Brin, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 40 days.

(21) Appl. No.: 12/047,482

(22) Filed: Mar. 13, 2008

(65) Prior Publication Data

US 2009/0232850 A1    Sep. 17, 2009

(51) Int. Cl.
  *A61K 39/08* (2006.01)
  *A61K 38/00* (2006.01)
  *A61P 19/02* (2006.01)

(52) U.S. Cl.
  USPC ............. 424/247.1; 424/239.1; 514/16.8

(58) Field of Classification Search
  None
  See application file for complete search history.

(56) References Cited

U.S. PATENT DOCUMENTS

| | | |
|---|---|---|
| 5,427,291 A | 6/1995 | Smith |
| 5,437,291 A | 8/1995 | Pasricha |
| 5,670,484 A | 9/1997 | Binder |
| 5,674,205 A | 10/1997 | Pasricha |
| 5,714,468 A | 2/1998 | Binder |
| 5,766,605 A | 6/1998 | Sanders |
| 5,989,545 A | 11/1999 | Foster |
| 6,063,768 A | 5/2000 | First |
| 6,113,915 A | 9/2000 | Aoki |
| 6,139,845 A | 10/2000 | Donovan |
| 6,143,306 A | 11/2000 | Donovan |
| 6,265,379 B1 | 7/2001 | Donovan |
| 6,299,893 B1 | 10/2001 | Schwartz |
| 6,306,403 B1 | 10/2001 | Donovan |
| 6,306,423 B1 | 10/2001 | Donovan |
| 6,312,708 B1 | 11/2001 | Donovan |
| 6,328,977 B1 | 12/2001 | Donovan |
| 6,358,513 B1 | 3/2002 | Voet |
| 6,358,917 B1 | 3/2002 | Carruthers |
| 6,358,926 B2 | 3/2002 | Donovan |
| 6,365,164 B1 | 4/2002 | Schmidt |
| 6,395,277 B1 | 5/2002 | Graham |
| 6,423,319 B1 | 7/2002 | Brooks |
| 6,458,365 B1 | 10/2002 | Aoki |
| 6,464,986 B1 | 10/2002 | Aoki |
| 6,623,742 B2 | 9/2003 | Voet |
| 6,767,544 B2 | 7/2004 | Brooks |
| 6,787,517 B1 * | 9/2004 | Gil et al. ........................ 514/1 |
| 6,838,434 B2 | 1/2005 | Voet |
| 6,869,610 B2 | 3/2005 | Aoki |
| 6,977,080 B1 | 12/2005 | Donovan |
| 7,048,927 B2 | 5/2006 | Brooks |
| 7,091,176 B2 | 8/2006 | Aoki |
| 7,223,399 B2 | 5/2007 | Brooks |
| 7,361,358 B2 | 4/2008 | Aoki |
| 7,485,624 B2 | 2/2009 | Donovan |
| 7,494,654 B2 | 2/2009 | Brooks |
| 2003/0165541 A1 * | 9/2003 | Donovan .................. 424/236.1 |
| 2004/0009180 A1 | 1/2004 | Donovan |
| 2004/0037865 A1 | 2/2004 | Miller |
| 2004/0086531 A1 | 5/2004 | Barron |
| 2005/0147626 A1 | 7/2005 | Blumenfeld |
| 2005/0191321 A1 | 9/2005 | Turkel |
| 2005/0266029 A1 * | 12/2005 | Aoki et al. ................ 424/239.1 |
| 2006/0083758 A1 | 4/2006 | Dadas |
| 2006/0121057 A1 * | 6/2006 | Turkel et al. ............. 424/239.1 |
| 2006/0216313 A1 | 9/2006 | Brooks |
| 2007/0048334 A1 | 3/2007 | Aurora |
| 2008/0057084 A1 * | 3/2008 | Burstein et al. .......... 424/239.1 |

FOREIGN PATENT DOCUMENTS

| | | |
|---|---|---|
| EP | 0 605 501 B1 | 7/1994 |
| WO | WO 95/17904 | 7/1995 |
| WO | WO 2004/041303 A1 | 5/2004 |

OTHER PUBLICATIONS

Callaway et al 2001 Seminars in Cutaneous Medicine and Surgery, vol. 20 No. 2 pp. 127-136.*
By Denise Mann Reviewed by Louise Chang 2006 WebMD, LLC. "Botox May Cut Knee Osteoarthritis Pain".*
"Arthritis Special Report 2007 Botox and Knee Osteoarthritis".*
U.S. Appl. No. 12/436,730, filed May 6, 2009, Brooks.
Ahuja, Vanita; et al.: Head and Neck Manifestations of Gastroesophageal Reflux Disease, American Family Physician, vol. 60, No. 3, Sep. 1, 1999.
Albanese, A.; et al.: The Use of Botulinum Toxin on Smooth Muscles, Eur J Neurol Nov. 1995;2(Supp 3):29-33.
Aoki K., et al, Mechanisms of the Antinociceptive Effect of Subcutaneous BOTOX ®: Inhibition of Peripheral and Central Nociceptive Processing, Cephalalgia Sep. 2003; 23(7):649.
Bigalke, H.; et al.: Botulinum A Neurotoxin Inhibits Non-Cholinergic Synaptic Transmission in Mouse Spinal Cord Neurons in Culture, Brian Research 360;318-324:1985.
Bigalke, H.; et al.: Tetanus Toxin and Botulinum A Toxin Inhibit Release and Uptake of Various Transmitters, as Studied with Particulate Preparations From Rat Brain and Spinal Cord, Naunyn Schmiedeberg's Arch Pharmacol 316;244-251:1981.

(Continued)

*Primary Examiner* — Vanessa L Ford
*Assistant Examiner* — Nina Archie
(74) *Attorney, Agent, or Firm* — Ted Chan; Brigitte Phan; Debra Condino

(57) ABSTRACT

Methods for treating a coronary risk factor (such as hypertension, diabetes, hyperlipidemia and obesity) and/or a respiratory disorder (such as asthma, chronic obstructive pulmonary disease and bronchitis) and/or arthritis by local administration of a botulinum neurotoxin to at least one of a head, neck or shoulder location (for example, by subdermal, subcutaneous or intramuscular administration of the botulinum neurotoxin) of a patient with a coronary risk factor, respiratory disorder or arthritis.

6 Claims, No Drawings

OTHER PUBLICATIONS

Binz T. et al.: The Complete Sequence of Botulinum Neurotoxin Type A and Comparison with Other Clostridial Neurotoxins, J. Biological Chemistry 265(16);9153-9158:1990.

Boyd R.S., et al.: The Effect of Botulinum Neurotoxin-B on Insulin Release From a β-cell Line, Mov Disord, 10(3):376:1995, Abstract 19.

Boyd R.S. et al.: The Insulin Secreting β-cell Line, HIT-15, Contains SNAP-25 which is a Target for Botulinum Neurotoxin-A, Mov Disord, 10(3):376:1995, Abstract 20.

Bushara K., Botulinum Toxin and Rhinorrhea, Otolaryngol Head Neck Surg 1996; 114(3):507.

Coffield, Eds. Jankovic J. et al.: Therapy With Botulinum Toxin, Marcel Dekker, Inc., (1994), Chapter 1.

Dykstra, D.D., et al.: Treatment of Detrusor-Sphincter Dyssynergia with Botulinum A Toxin: A Double Blind Study, Arch Phys Med Rehabil Jan. 1990; 71:24-6.

Eaker, E.Y., et al.: Untoward Effects of Esophageal Botulinum Toxin Injection in the Treatment of Achalasia, Dig Dis Sci Apr. 1997;42(4):724-7.

Friedenberg, Frank; et al.: The Use of Botulinum Toxin for the Treatment of Gastrointestinal Motility Disorders. Digestive Diseases and Sciences, vol. 49, No. 2 Feb. 2004.

Gonelle-Gispert, C., et al.: SNAP-25a and -25b Isoforms are Both Expressed in Insulin-Secreting Cells and Can Function in Insulin Secretion, Biochem J. 1;339 (pt 1):159-165:1999.

Gui D., et al.: Botulinum Toxin Injected in the Gastric Wall Reduces Body Weight and Food Intake in Rats, Aliment Pharmacol Ther Jun. 2000; 14(6):829-834.

Gui D., et al.: Effects of Botulinum Toxin on Gastric Emptying and Digestive Secretions. A Possible Tool for Correction of Obesity?, Naunyn Schmiedebergs Arch Pharmacol Jun. 2002; 365(Suppl 2):R22.

Habermann E., et al.: Tetanus Toxin and Botulinum A and C Neurotoxins Inhibit Noradrenaline Release From Cultured Mouse Brain, J. Neurochem 51(2); 522-527:1988.

Habermann E., Inhibition by Tetanus and Botulinum A Toxin of the Release of [$^3$H]Noradrenaline and [$^3$H]GABA From Rat Brain Homogenate, Experientia 44; 224-226:1988.

Habermann, ($^{125}$I-Labelled Neurotoxin From Clostridium Botulinum A: Preparation, Binding to Synaptosomes and Ascent to the Spinal Cord, Naunyn-Schmiedeberg's Arch. Pharmacol. 1974; 281, 47-56.

Harrison's Principles of Internal Medicine (1998), Edited by Anthony Fauci et al., 14$^{th}$ edition, Published by McGraw Hill.

Katsambas A., et al.: Cutaneous Diseases of the Foot: Unapproved Treatments, Clin Dermatol Nov.-Dec. 2002;20(6):689-699.

Keir, James, Botulinum Toxin-Physiology and Applications in Head and Neck Disorders, Neck & Head, Jun. 2005, pp. 525-535.

Khawaja, Hassan Abbas; et al.: Botox in Dermatology, International Journal of Dermatology 2001, 40, 311-317).

Kohl A., et al.: Comparison of the Effect of Botulinum Toxin A (Botox ®) with the Highly-Purified Neurotoxin (NT 201) in the Extensor Digitorum Brevis Muscle Test, Mo. Disord. 2000; 15(Suppl 3): 165.

Kondo T., et al.: Modification of the Action of Pentagastrin on Acid Secretion by Botulinum Toxin, Experientia 1977;33:750-751.

Kumar R and Seeberger LC: Long-term Safety, Efficacy, and Dosing of Botulinum Toxin Type B (Myobloc ®) in Cervical Dystonia (CD) and Other Movement Disorders. Mov Disord 2002;17(Suppl 5):S292-S293.

Lacy, Brian E., et al., The Treatment of Diabetic Gastroparesis with Botulinum Toxin Injection of the Pylorus, Diabetes Care, vol. 27, No. 10, Oct. 2004, pp. 2341-2347.

Li Y, et al., Sensory and Motor Denervation Influences Epidermal Thickness in Rat Foot Glabrous Skin, Exp Neurol 1997; 147:452-462 (see p. 459).

Marjama-Lyons, J., et al.: Tremor-Predominant Parkinson's Disease, Drugs & Aging 16(4);273-278:2000.

Meyer K.E. et al.: A Comparative Systemic Toxicity Study of Neurobloc in Adult Juvenile Cynomolgus Monkeys, Mov. Disord 15(Suppl 2);54;2000.

Miller, Larry S., et al.: Treatment of Idiopathic Gastroparesis with Injection of Botulinum Toxin into the Pyloric Sphincter Muscle, The American Journal of Gastroenterology, vol. 97, No. 7, 2002, pp. 1653-1660.

Moyer E. et al.: Botulinum Toxin Type B: Experimental and Clinical Experience, Chapter 6, pp. 71-85 of "Therapy With Botulinum Toxin", Edited by Jankovic, J. et al. (1994), Marcel Dekker, Inc.

Naumann M., et al.: Botulinum Toxin Type A in the Treatment of Focal, Axillary and Palmar Hyperhidrosis and Other Hyperhidrotic Conditions, European J. Neurology 6 (Supp 4): S111-S115: 1999.

Payne M., et al.: Botulinum Toxin as a Novel Treatment for Self Mutilation in Lesch-Nyhan Syndrome, Ann Neurol Sep. 2002;52(3 Supp 1):S157).

Pearce, L.B., Pharmacologic Characterization of Botulinum Toxin for Basic Science and Medicine, Toxicon 35(9); 1373-1412 at 1393, Sep. 1997;35(9).

Qureshi, Waqar: Gastrointestinal Uses of Botulinum Toxin, Journal of Clincial Gastroenterol, 200;34(2): 126-128), Feb. 2002;34(2).

Ragona, R.M., et al.: Management of Parotid Sialocele with Botulinum Toxin, The Laryngoscope 109:1344-1346:1999.

Rogers J., et al.: Injections of Botulinum Toxin A in Foot Dystonia, Neurology Apr. 1993;43(4 Supp 2).

Rohrbach S., et al.: Botulinum Toxin Type A Induces Apoptosis in Nasal Glands of Guinea Pigs, Ann Otol Rhinol Laryngol Nov. 2001;110(11):1045-1050.

Rohrbach S., et al.: Minimally Invasive Application of Botulinum Toxin Type a in Nasal Hypersecretion, J Oto-Rhino-Laryngol Nov.-Dec. 2001; 63(6):382-384.

Rossi S., et al.: Immunohistochemical Localization of SNAP-25 Protein in the Stomach of Rat, Naunyn Schmiedebergs Arch Pharmacol 2002;365(Suppl 2):R37.

Sanchez-Prieto, J., et al.: Botulinum Toxin A Blocks Glutamate Exocytosis From Guinea Pig Cerebral Cortical Synaptosomes, Eur J. Biochem 165;675-681:1987.

Schantz E.J., et al.: Preparation and Characterization of Botulinum Toxin Type A for Human Treatment (in Particular pp. 44-45), Chapter 3 of Janovic, J., et al, Therapy with Botulinum Toxin, Marcel Dekker, Inc (1994).

Schantz, E.J., et al.: Properties and Use of Botulinum Toxin and Other Microbial Neurotoxins in Medicine, Microbiol Rev. 56;80-99:1992.

Sevim, S., et al.: Botulinum Toxin—A Therapy for Palmar and Plantar Hyperhidrosis Acta Neurol Belg Dec. 2002;102(4):167-170.

Singh, Critical Aspects of Bacterial/Protein Toxins, pp. 63-84 (Chapter 4) of Natural Toxins II, Edited by B.R. Singh et al., Plenum Press, New York (1996).

Sloop, Richard R.; et al.: Reconstituted Botulinum Toxin Type A Does Not Lose Potency in Humans If it is Refrozen or Refrigerated for 2 Weeks Before use, Neurology, 48:249-253:1997.

Spierings, ELH; et al.: Reflux-Triggered Migrained Headache Originating from the Upper Gum/Teeth Cephalalgia, 2002, 22, p. 555-556).

Suputtitada, A., Local Botulinum Toxin Type A Injections in the Treatment of Spastic Toes, Am J Phys Med Rehabil Oct. 2002;81(10):770-775).

Tacks, L., et al.: Idiopathic Toe Walking: Treatment with Botulinum Toxin A Injection, Dev Med Child Neurol 2002;44(Suppl 91):6).

Thumshirn et al (Schweiz Rundsch Med Prax., Oct. 16, 2002;91(42):1741-7).

Wang Z., et al.: Effects of Botulinum Toxin on Gastric Myoeletrical and Vagal Activities in Dogs, Gastroenterology Apr. 2001;120(5 Suppl 1):A-718.

Weigand et al.: $^{125}$I-labelled Botulinum A Neurotoxin:Pharmacokinetics in Cats After Intramuscular Injection, Nauny-Schmiedeberg's Arch. Pharmacol. 1976;292, 161-165.

Wiesel P.H. et al.: Botulinum Toxin for Refractory Postoperative Pyloric Spasm, Endoscopy 1997;29(2):132.

Zhao, Xiaotuan, et al.: Botulinum Toxin for Spastic Gi Disorders: A Systematic Review, Gastrointestinal Endoscopy, vol. 57, No. 2, 2003, pp. 219-235.

* cited by examiner

THERAPEUTIC TREATMENTS USING BOTULINUM NEUROTOXIN

BACKGROUND

The present invention relates to therapeutic methods utilizing a botulinum neurotoxin such as for treating cardiac risk factors (e.g. hypertension, diabetes, hyperlipidemia, and obesity) and/or respiratory disorders (e.g. asthma, bronchitis and chronic obstructive pulmonary disease (COPD)) and/or arthritis. More particularly, the present invention relates to methods for treating various cardiac risk factors and/or respiratory disorders and/or arthritis utilizing local administration of at least one botulinum neurotoxin.

Coronary Risk Factors

A coronary (or cardiac) risk factor is a condition and/or behavior that increases a patient's chances of developing a coronary heart disease. A coronary heart disease is also called coronary artery disease (CAD), ischaemic heart disease or atherosclerotic heart disease and is the end result of the accumulation of atheromatous plaques in walls of the arteries that supply heart muscle with oxygen and nutrients. The fewer total number of risk factors that a patient has, the less risk the patient has of developing a coronary heart disease. Additionally, the greater the level of a particular risk factor (i.e. a clinically measurable aspect of the risk factor, for example having a total blood cholesterol level of 200 mg/dL or greater rather than below 200 mg/dL), the greater is the risk that the patient will develop a coronary heart disease.

Some coronary risk factors cannot be controlled. Examples of uncontrollable coronary risk factors include, for example, age and genetic disposition. The risk of developing some coronary heart disease simply increases with every passing year. For example men ages 45 and older and women ages 55 and older are at increased risk of developing coronary heart disease as compared to younger persons. Another factor to consider is family history. If a person is the child of parents who developed coronary heart disease before the age of 55, such offspring are more likely to develop coronary heart disease themselves than their peers whose parents developed coronary heart disease after the age 55 or not at all. Lastly, studies have shown a person's racial or ethnic background can also be considered a risk factor for developing coronary heart disease, where African Americans, Mexican Americans, American Indians, and other Native Americans are at greater risk than Caucasians.

Some coronary risk factors can be controlled. Examples of controllable coronary risk factors include physical inactivity, smoking, being overweight or obese, hypertension (high blood pressure), high blood cholesterol and having diabetes. People with inactive lifestyles simply have an increased risk of developing heart disease at some point in their life. In order to reduce this risk, it is generally advised that a person participate in 30-60 minutes of physical activity on most days. People who smoke cigarettes have the greatest risk among the general population of smokers (smoking being a risk factor in and of itself, as it interferes with the ability of the body to prevent blood clotting), with those who smoke cigars or pipes having a risk of developing coronary heart disease that is less than those that smoke cigarettes. Even if one does not smoke, exposure to other people's second-hand smoke increases the risk of developing cardiovascular disease. Naturally then, it follows that quitting smoking helps to reduce the risk of developing and suffering coronary heart disease.

Being overweight and/or obese is also a coronary risk factor for developing coronary heart disease. Persons having too much body fat are at an increased risk for developing coronary heart disease and/or eventually experiencing a cardiac event, including instant death or a nonfatal infarction. In particular, women with waist measurements of more than 35 inches and men with waist measurements of more than 40 inches (having too much fat around the waist), increases that person's risk of developing heart disease. Another method to measure if a person is at risk is to determine their Body Mass Index (BMI). A BMI number is a number calculated and based upon a person's weight and height. For most people, the BMI number is a reliable indicator of the amount of fat the person carries, and is typically used by health care professionals to screen for weight categories that may lead to health problems, such as diabetes and coronary heart disease. Persons having a BMI value of 25 or greater are considered to be at the highest risk of developing coronary heart disease.

Hypertension, or high blood pressure, is blood pressure of about 140/90 mmHg or higher. Nearly 1 in 3 American adults has high blood pressure. Unfortunately, many people that suffer from high blood pressure are unaware they have elevated pressures until they experience trouble with their heart, brain, or kidneys. If not treated, hypertension can lead to heart enlargement, aneurysms in blood vessels such as at the aorta and arteries in the brain, legs, and intestines. Furthermore, hypertension can lead to blood vessel narrowing in the kidney, which may cause a kidney to fail. Additionally and as stated above, hypertension is one of the many coronary risk factors, and can lead to hardening of the arteries in the body, especially those in the heart, brain and kidneys which can lead to a heart attack, a stroke, or kidney failure.

Having high blood cholesterol and/or high triglyceride levels are additional coronary risk factors. The term hyperlipidemia means high lipid levels, and while hyperlipidemia includes several conditions, it usually means that a patient has high cholesterol and high triglyceride levels. Persons having total blood cholesterol level of 200 mg/dL (milligrams/per deciliter) or higher and/or triglyceride levels above 150 mm/dL have increased risk for developing coronary heart disease. People that already have other risk factors and have low-density lipoprotein (LDL) cholesterol levels of 100 mg/dL or higher are at increased risk also. Persons with no other risk factors but having low-density lipoprotein (LDL) levels of 160 mg/dL or higher, and/or with high-density lipoprotein (HDL) cholesterol levels of less than 40 mg/dL, are also considered to have an increased risk of developing coronary heart disease. Commonly prescribed statins (or HMG-CoA reductase inhibitors) are a class of drugs that are used to lower cholesterol levels in people with or at risk of cardiovascular disease. Cholesterol is lowered by inhibition of HMG-CoA reductase, which is the rate-limiting enzyme of the pathway of cholesterol synthesis, which stimulates LDL receptors, resulting in an increased clearance of low-density lipoprotein (LDL) from the bloodstream and a decrease in blood cholesterol levels. Additionally, maintaining a "heart-healthy" diet and increased exercise is also advised to patients having high blood cholesterol and/or high triglyceride levels.

Diabetes is another coronary risk factor. Diabetes mellitus is a chronic disease in which blood glucose (sugar) levels are too high. Normal regulation of the hormone, insulin, is responsible for maintaining proper glucose levels in the blood. Abnormally high levels of glucose can damage the small and large blood vessels, leading to diabetic blindness, kidney disease, amputations of limbs, stroke, and heart disease. Generally, there are two types of diabetes, Type 1 diabetes is usually (but not always) diagnosed in children and young adults. The islets of Langerhans, in the pancreas of people who have type 1 diabetes, do not produce insulin, and thus such people rely on external insulin, typically injected subcutaneously or as recently developed inhaled. People with type 2 diabetes mellitus have insulin resistance, not enough insulin (low insulin production), or both; they may or may not eventually require externally supplied insulin to control their glucose levels and can take oral, systemic medication such as, metformin (FORTAMET, GLUCOPHAGE, and RIOMET). About 17 million people in America have Diabetes mellitus, and about 1 million new cases are diagnosed each year.

Respiratory Disorders

It has been estimated that about 350,000 people in the United States die from lung disease and that lung disease is the number three killer in America, responsible for one in seven deaths. About 25 million Americans live with chronic lung disease, which affect people of all ages and genders.

Bronchitis, asthma and chronic obstructive pulmonary disease (COPD) are example of some respiratory disorders.

Chronic obstructive pulmonary disease (COPD) is a chronic lung disease, marked by damage to the lungs and includes two main illnesses: chronic bronchitis and emphysema, both of which make breathing difficult. In COPD, the respiratory airways and air sacs (alveoli) lose their shape, become slack and in some cases, the walls between sacs are even destroyed. Additionally, excessive mucus is produced in the airways, as well as the walls of the airways become inflamed and thickened. As a result, less air gets in and less air goes out of the lungs. Unfortunately, there is no cure for COPD.

Cigarette smoking is the most common cause of COPD, and breathing other kinds of lung irritants such as pollution, dust, or chemical fumes over a long period of time may also cause or contribute to COPD.

Bronchitis is an inflammation of the bronchi (medium-size airways) in the lungs which can be acute (e.g. caused by a virus, bacteria, dust and fumes) or chronic. In persons with chronic bronchitis, the bronchial tubes become permanently thickened and/or inflamed. The patient with chronic bronchitis typically exhibits a persistent, continuous cough with mucus. A person is diagnosed as having chronic bronchitis if they cough most days for at least three months a year in two consecutive years. Smoking, air pollution and dust or toxic gases can contribute to the chronic bronchitis. In some instances, chronic inflammation of the airways may lead to asthma. Typical treatment includes antibiotics (if bacterial), rest, ingestion of copious amounts of fluids, and over-the-counter cough medication.

Asthma is typically an allergic disorder of respiration, characterized by bronchospasm, wheezing, and difficulty in expiration. It can also be accompanied by coughing and feelings of chest constriction. Asthma occurs when the main bronchial tubes are inflamed, resulting in a tightening of the muscles of the bronchial walls, and can be accompanied by excessive mucus production. As a result, wheezing up to and including severe difficulty in breathing can be brought on. In some instances the severity of the constriction is such that the person experiences an asthma attack, which can be life-threatening.

The signs of asthma and symptoms can vary from person to person and from episode to episode and can range from mild to severe. Occasional asthma episodes with mild, short-lived symptoms such as wheezing can be experienced wherein between episodes no difficulty in breathing is experienced. Other asthma sufferers may experience chronic coughing and wheezing punctuated by severe asthma attacks, which are typically preceded by warning signs, such as increased shortness of breath or wheezing, coughing, chest tightness or pain. In children, an audible whistling or wheezing sound when exhaling can sometimes be heard, even without a stethoscope (especially after vigorous activities e.g. running, playing, climbing etc. . . . ) and frequent coughing spasms.

Medications to treat asthma vary from person to person. In general, a combination of long-term control medications and quick relief medications is typically utilized. Medications generally fall into one of three categories: long-term-control medications, quick-relief medications and medications for allergy-induced asthma. Long-term control medications are usually taken every day on a long-term basis, to control persistent asthma, while quick relief medications are utilized to relieve symptoms of short-term, asthma attacks. For allergy-induced asthma, medications are taken to decrease a person's sensitivity to a particular allergen and prevent or decrease an immune system reaction to a particular allergen or allergens.

Exemplary long term medications to treat asthma include inhaled corticosteroids which are anti-inflammatory drugs that reduce inflammation in the airways and prevent blood vessels from leaking fluid into the airway tissues. Exemplary inhaled corticosteroids include fluticasone (FLOVENT), budesonide (PULMICORT), triamcinolone (AZMACORT), flunisolide (AEROBID) and beclomethasone (QVAR). Another long-term medication are the long-acting beta-2 agonists (LABAs), bronchodilators that dialate constricted airways. Examples include salmeterol (SEREVENT DISKUS) and formoterol (FORADIL). Still additional long term medications include leukotriene modifiers, which reduce the production or block the action of leukotrienes, which are release by cells in the lungs during an asthma attack. Leukotrienes release results in inflamed airways, leading to wheezing, mucus overproduction and coughing. Exemplary leukotriene modifiers include montelukast (SINGLULAIR) and zafirlukast (ACCOLATE).

Additional long term medications to treat asthma include cromolyn (INTAL) and nedocromil (TILADE), which require daily inhaled use, to help prevent attacks of mild to moderate asthma. Theophylline (dimethylxanthine) requires daily administration, which is a bronchodilator in pill form.

Quick-relief medications are typically short active bronchodilators which are designed to address the symptoms of an oncoming or in progress asthma attack. Examples of quick-relief medications include short-acting beta-2 agonists, such as albuterol, prednisone, methylprednisolone and hydrocortisone.

Allergy-desensitization shots (immunotherapy) can also be utilized, where a series of therapeutic injections containing small doses of those allergens. These injections are administered once a week for a few months, then once a month for a period of three to five years, the theory being that over time, the patient will lose their sensitivity to the allergens. Additionally, blocking the action of human immunoglobulin E (IgE), which is commonly involved with allergies when present in high amounts in the body, is still another route for treating asthma. Omalizumab (marketed under the name XOLAIR) is a monoclonal antibody made by Genentech/Novartis and used mainly in allergy-related asthma therapy, with the purpose of reducing allergic hypersensitivity. XOLAIR (omalizumab) is a recombinant DNA-derived humanized IgG1k monoclonal antibody that selectively binds to human immunoglobulin E (IgE), and limits the degree of release of mediators of the allergic response, and thus attenuates the asthmatic response.

Arthritis

Arthritis is a joint disorder that results in inflammation at an area of a patient where two different bones meet. As such, arthritis is typically accompanied by joint pain, that can be the result of wear and tear of cartilage (e.g. osteoarthritis) to pain associated with inflammation resulting from an overactive immune system (e.g. rheumatoid arthritis). Arthritis is classified as a rheumatic disease and as such affects joints, muscles, ligaments, cartilage, tendons, and may have the potential to affect internal body organs.

Rheumatoid arthritis (RA) is a long-term disease that causes inflammation of the joints and surrounding tissues and may affect other organs/tissues depending on the patient. RA is considered an autoimmune disease, and it appears to affected women more often than men. Joints of the extremities (i.e. arms and legs) are most commonly affected and including but limited to the wrists, fingers, knees, feet, and ankles.

Symptoms of arthritis include inflammation; pain and limited joint function e.g., joint stiffness, swelling, redness, and warmth. In persons suffering RA, symptoms in some patients can include fever, joint swelling, fatigue, and pain in various organs such as the lungs, heart, or kidneys.

Various treatment options are typically utilized to treat arthritis and include NSAIDs (nonsteroidal anti-inflammatory drugs), COX-2 inhibitors, various analgesics and corticosteroids. In some instances, a physician may choose to directly inject a medicament into the affected joint. This is known as viscosupplementation, and involves injection of gel-like substances (hyaluronates) into the subject a joint to supplement the viscous properties of synovial fluid in the joint. For example, SYNVISC® is an FDA-approved elastic and viscous substance made from hyaluronan that is injected into the knee to provide pain relief from osteoarthritis.

Clostridial Toxins

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

About 50 picograms of a commercially available botulinum toxin type A (a purified neurotoxin complex available from Allergan, Inc., of Irvine, Calif. under the tradename BOTOX® in 100 unit vials) is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 1 2 million times more lethal than cholera. Singh, Critical Aspects of Bacteria/Protein Toxins, pages 63-84 (chapter 4) of Natural Toxins II, edited by B. R. Singh et al., Plenum Press, New York (1976) (where the stated $LD_{50}$ of botulinum toxin type A of 0.3 ng equals 1 unit is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type 8: Experimental and Clinical Experience*, being chapter 6, pages 71-85 of "Therapy With Botulinum Toxin," edited by Jankovic, J. et al. (1994), Marcel Dekker, Inc. Botulinum toxin apparently binds with high affinity to cholinergic motor neurons, is translocated into the neuron, and blocks the release of acetylcholine. Additional uptake can take place through low affinity receptors, as well as by phagocytosis and pinocytosis.

Regardless of stereotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface. In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{2+}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G, cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). Almost twenty years ago, in 1989, a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxin serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65.1999, and *MovDisord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule, and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain J* Neurochem 51(2); 522-527:1988)), CGRP, substance P, and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897). Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1 373-1 412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [3H] Noradrenaline and [3H] GABA From Rat Brain Homogenate*, Experientia 44; 224-226: 1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 31 6; 244-251:1 981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype, only cleave a portion of the toxin produced. The exact proportion of nicked to unnicked molecules depends on the length of incubation and the temperature of the culture. Therefore, a certain percentage of any preparation of, for example, the botulinum toxin type B toxin, is likely to be inactive, possibly accounting for the known significantly lower potency of botulinum toxin type B, as compared to botulinum toxin type A (and thus the routine use of many thousands of units of botulinum toxin type B, as known in the art, see e.g. "Long-term safety, efficacy, and dosing of botulinum toxin type B (MYOBLOC®) in cervical dystonia (CD) and other movement disorders" Kumar R and Seeberger L C. Mov Disord 2002; 17(Suppl 5):S292-S293). The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $>3 \times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botuilnum toxin and Other Microbial Neurotoxins in Medicine*, Microbiol Rev. 56;

80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1\text{-}2\times10^8$ $LD_{50}$ U/mg or greater; purified botulinum toxin type B with an approximately 156 kD molecular weight with a specific potency of $1\text{-}2\times10^8$ $LD_{50}$ U/mg or greater; and purified botulinum toxin type F with an approximately 155 kD molecular weight with a specific potency of $1\text{-}2\times10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition for use in accordance with the present disclosure.

As with enzymes generally, the biological activities of botulinum toxins (which are intracellular peptidases) is dependant, at least in part, upon their 3-dimensional conformation. Thus, botulinum toxin type A is detoxified by heat, various chemicals, surface stretching, and surface drying. Additionally, it is known that dilution of the toxin complex obtained by the known culturing, fermentation and purification to the much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. Botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 U of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks (*Neurology*, 48:249-53, 1997). It has been reported that botulinum toxin type A has been used in clinical settings as follows:

(1) about 75-125 U of BOTOX® per intramuscular injection (multiple muscles) to treat cervical dystonia;
(2) 5-10 U of BOTOX® per intramuscular injection to treat glabellar lines (brow furrows) (5 units injected intramuscularly into the procerus muscle and 10 units injected intramuscularly into each corrugator supercilii muscle);
(3) about 30-80 U of BOTOX® to treat constipation by intrasphincter injection of the puborectalis muscle;
(4) about 1-5 Upper muscle of intramuscularly injected BOTOX® to treat blepharospasm by injecting the lateral pre-tarsal orbicularis oculi muscle of the upper lid and the lateral pre-tarsal orbicularis oculi of the lower lid;
(5) to treat strabismus, extraocular muscles have been injected intramuscularly with between about 1-5 U of BOTOX®, the amount injected varying based upon both the size of the muscle to be injected and the extent of muscle paralysis desired (i.e. amount of diopter correction desired);
(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session;
(7) to treat migraine, pericranial (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S11-S1 150: 1999), and in some circumstances for as long as 27 months, when used to treat glands, such as in the treatment of hype rhydrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of effect of an intramuscular injection of BOTOX® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and DYSPORT® available from Beaufour Ipsen, Porton Down, England. A botulinum toxin type B preparation (MYOBLOC®) is available from Solstice Pharmaceuticals of San Francisco, Calif.

A botulinum toxin has also been proposed for or has been used to treat otitis media of the ear (U.S. Pat. No. 5,766,605), inner ear disorders (U.S. Pat. Nos. 6,265,379; 6,358,926), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. Nos. 6,139,845), smooth muscle disorders (U.S. Pat. No. 5,437,291), and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805). U.S. Patent Application Publication 2007/0048334 A1, Ser. No. 11/211,311 and filed Aug. 24, 2005, discloses the use of a botulinum toxin to improve gastric emptying and/or treating gastroesophageal reflux disease (GERD) by administration to a patient's head, neck and shoulder muscles. It is known that a botulinum toxin can be used to weaken the chewing or biting muscle of the mouth so that self inflicted wounds and resulting ulcers can heal (Payne M., et al, Botulinum toxin as a novel treatment for self mutilation in Lesch-Nyhan syndrome, Ann Neurol 2002 September; 52(3 Supp 1):S157).). U.S. Patent Application Publication 20050191321 A1, Ser. No. 11/039,506 and filed Jan. 18, 2004, discloses treating medication overuse disorders (MOD), by local administration of a Clostridial toxin. U.S. Patent Application Publication 20050147626 A1, Ser. No. 10/964,898 and filed Oct. 12, 2004 discloses treating or preventing, by peripheral administration of a botulinum toxin to or to the vicinity of a trigeminal sensory nerve, a neurological disorder and/or a neuropsychiatric disorder.

Additionally, a botulinum toxin may have an effect to reduce induced inflammatory pain in a rat formalin model. Aoki K., et al, Mechanisms of the antinociceptive effect of subcutaneous BOTOX®: Inhibition of peripheral and central nociceptive processing, Cephalalgia 2003 September; 23(7): 649. Furthermore, it has been reported that botulinum toxin nerve blockage can cause a reduction of epidermal thickness. Li Y, et al., Sensory and motor denervation influences epidermal thickness in rat foot glabrous skin, Exp Neurol 1997; 147:452-462 (see page 459). U.S. Patent Application Publication 20050266029 A1, Ser. No. 11/159569 and filed on Jun. 22, 2005 relates to methods for treating pain associated with arthritis. Finally, it is known to administer a botulinum toxin to the foot to treat excessive foot sweating (Katsambas A., et al., Cutaneous diseases of the foot: Unapproved treatments, Clin Dermatol 2002 November-December; 20(6):689-699; Sevim, S., et al., Botulinum toxin-A therapy for palmar and plantar hyperhidrosis, Acta Neurol Belg 2002 December; 102(4):167-70), spastic toes (Suputtitada, A., Local botulinum toxin type A injections in the treatment of spastic toes, Am J Phys Med Rehabil 2002 October; 81(10):770-5), idiopathic toe walking (Tacks, L., et al., Idiopathic toe walking: Treatment with botulinum toxin A injection, Dev Med Child Neurol 2002; 44(Suppl 91):6), and foot dystonia (Rogers J., et al., Injections of botulinum toxin A in foot dystonia, Neurology 1993 April; 43(4 Suppl 2)). Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively).

Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Additionally, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., The Complete Sequence of Botulinum Neurotoxin Type A and Comparison with Other Clostridial Neurotoxins, J Biological Chemistry 265(16); 9153-9158: 1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

What is needed therefore are effective and efficient methods for treating arthritis, respiratory disorders, such as COPD, asthma, bronchitis and for treating/alleviating (e.g. lowering) coronary risk factors, such as hypertension, high cholesterol, high triglyceride levels, diabetes, hyperlipidemia, and obesity that do not require daily administration and/or strict patient compliance.

SUMMARY

The present invention meets this need and provides methods for treating a respiratory disorder and/or arthritis or and/or coronary risk factor by intramuscular, subcutaneous or intradermal administration of a botulinum toxin to at least one of a head or neck and shoulder location of a patient in need thereof, that is, a patient with a respiratory disorder and/or arthritis and/or a coronary risk factor. Intracranial administration of a botulinum neurotoxin, that is, administration within the cranium and into brain tissue, is specifically excluded from the scope of the present invention.

According to one aspect of the present invention, the botulinum toxin is one of the botulinum toxin types A, B, $C_1$, D, E, F and G and is preferably botulinum toxin type A. The botulinum toxin (as a complex or as a pure, about 150 kDa protein) can be formulated with the excipient (such as an albumin) in an amount of between about 1 unit and about 25,000 units of the botulinum toxin. Preferably, the quantity of the botulinum toxin administered is between about 5 units and about 1500 units of a botulinum toxin type A. Where the botulinum toxin is botulinum toxin type B, preferably, the quantity of the botulinum toxin associated with the carrier can be between about 250 units and about 25,000 units of a botulinum toxin type B.

The amount of a botulinum toxin administered within the scope of the present invention during a given period can be between about $10^{-3}$ U/kg and about 35 U/kg per patient weight for a botulinum toxin type A and up to about 1500 U/kg per patient weight for other botulinum toxins, such as a botulinum toxin type B.

Preferably, the amount of a type A botulinum toxin administered is between about $10^{-2}$ U/kg and about 25 U/kg. Preferably, the amount of a type B botulinum toxin administered during a given period is between about $10^{-2}$ U/kg and about 1000 U/kg. More preferably, the type A botulinum toxin is administered in an amount of between about $10^{-1}$ U/kg and about 15 U/kg. Most preferably, the type A botulinum toxin is administered in an amount of between about 1 U/kg and about 10 U/kg. In many instances, administration of from about 1 unit to about 500 units of a botulinum toxin type A can provide effective and long lasting therapeutic relief. More preferably, from about 5 units to about 300 units of a botulinum toxin, such as a botulinum toxin type A, can be used and most preferably, from about 10 units to about 200 units of a neurotoxin, such as a botulinum toxin type A, can be locally administered into a target tissue with efficacious results. In a particularly preferred embodiment of the present invention, from about 20 units to about 300 units of a botulinum toxin, such as botulinum toxin type A, can be administered with therapeutically effective results.

The botulinum toxin can be made by *Clostridium botulinum*. Additionally, the botulinum toxin can be a modified botulinum toxin, that is, a botulinum toxin that has at least one of its amino acids deleted, modified or replaced, as compared to the native or wild type botulinum toxin. Furthermore, the botulinum toxin can be a recombinant produced botulinum toxin or a derivative or fragment thereof.

A method herein disclosed can be carried out by administration of a botulinum toxin to a patient in need thereof, i.e., having a coronary risk factor and/or arthritis and/or a respiratory disorder to be treated. Notably, the botulinum toxin is administered to a head, neck or shoulder location of a patient to provide a therapeutic effect upon the arthritis, coronary risk factor or respiratory disorder. Thus, the botulinum toxin is not administered so as to provide a therapeutic effect at the local site of administration of the botulinum toxin. Quiet the contrary i.e. administration of a botulinum toxin (as by intramuscular administration) to a head, neck or shoulder location (e.g. to an intramuscular site to one or more of the well known frontalis muscle, glabellar muscle, occipitalis muscle, temporalis muscle, masseter muscle, trapezius muscle, semispinalis muscle and splenius capitis muscles, and/or subcutaneously or intradermally at or in the vicinity of these muscles) has a therapeutic effect, as determined by alleviation of at least one symptom associated with arthritis, coronary risk factor or a respiratory disorder.

The botulinum toxin (as either a complex or as a pure [i.e. about 150 kDa molecule] can be a botulinum toxin A, B, C, D, E, F or G. Administration of the botulinum toxin in accordance with the instant disclosure can be by a transdermal route (i.e. by application of a botulinum toxin in a cream, patch or lotion vehicle), subdermal route (i.e. subcutaneous or intramuscular), or intradermal route of administration to at least one of a patient's head, neck or shoulder.

A hypothesized physiological reason for the efficacy of my invention is that the head, neck and/or administration of a botulinum toxin according to my invention reduces, inhibits and/or eliminates sensory input (afferent) from peripheral location(s) of the head and/or neck and/or shoulder into the central nervous system (including to the brain) which input kindles, generates, exacerbates and/or facilitates development, worsening or maintenance of a coronary risk factor, arthritis, or a respiratory disorder in a patient.

A particular dose of a botulinum used in a particular patient according to the present invention is typically less than the amount of a botulinum toxin that would be used to paralyze (i.e. result in complete loss of function or tone of a muscle) a muscle, since an intent of a method according to the present invention is not to paralyze a muscle but to reduce a sensory output from sensory neurons located in or on a muscle, or in or under the skin. As medicaments are typically utilized in the art, botulinum neurotoxin is administered to a particular patient at a starting amount, after which the patient is follow up with and any beneficial effect is noted. If no change and no adverse effect to the administered toxin is observed, the attending medical profession may choose to increase the dose of toxin administered and/or alter the location(s) of administration of the toxin.

The present invention encompasses a method for treating arthritis, a coronary risk factor or a respiratory disorder by administering a botulinum toxin to a head and/or neck and/or shoulder location of a patient with arthritis and/or coronary risk factor and/or a respiratory disorder, thereby treating the arthritis, coronary risk factor or a respiratory disorder. The botulinum toxin can be a botulinum toxins types A, B, $C_1$, D, E, F or G. Most preferably, the botulinum toxin is a botulinum toxin type A. The botulinum toxin administered can be a botulinum toxin complex (i.e. from about 300 kDa to about 900 kDa in molecular weight) or a pure botulinum toxin, that is, the about 150 kDa neurotoxic component of a botulinum toxin complex.

The coronary risk factor to be treated can be hypertension, diabetes, hyperlipidemia, and obesity, for example. The respiratory disorder treated can be, for example, asthma, bronchitis and chronic obstructive pulmonary disease.

Administration of a botulinum toxin according to the method disclosed herein can be by intramuscular or subdermal administration of the botulinum toxin to a head and/or neck and/or shoulder muscle of the patient. In some embodiments the patient can have a coronary risk factor and/or a respiratory disorder and/or arthritis as well as a headache, such as a tension headache, migraine (episodic or chronic), hormonal headache, cluster headache, sinus headache and cervogenic headache. A patient is said to suffer from chronic migraine headache when experiencing a migraine headache for fifteen days or greater per month, while a patient that suffers between 0 to eight days of migraine headaches per month is considered to suffer from episodic migraines.

In one aspect, a method for treating a respiratory disorder in a patient in need thereof comprises the step of administering a botulinum toxin to at least one of a head, neck or shoulder location of the patient with a respiratory disorder to thereby alleviate at least one symptom of the respiratory disorder and treat the respiratory disorder. In a particular embodiment, the administration step is carried out by intramuscular administration of the botulinum toxin to a muscle at the at least one of the head, neck or shoulder location of the patient.

Exemplary coronary risk factors that can be alleviated and treated in accordance with the instant disclosure include hypertension, diabetes, hyperlipidemia and obesity, for example.

In some embodiments the botulinum toxin is a botulinum toxin type A or B and is administered to a muscle selected from the group consisting of a frontalis muscle, a glabellar muscle, an occipitalis muscle, a temporalis muscle, a masseter muscle, a trapezius muscle, a semispinalis muscle and a splenius capitis muscle. The locations of all of these muscles are well known to those of ordinary skill in the art, and can easily be found in any of several medical anatomy texts, for example.

In still other embodiments, a method for treating arthritis in a patient in need thereof comprises the step of intramuscular administration of a therapeutically effective amount of a botulinum neurotoxin, such as toxin type A or a botulinum toxin type B, to at least one muscle selected from the group consisting of a frontalis muscle, glabellar muscle, occipitalis muscle, temporalis muscle, masseter muscle, trapezius muscle, semispinalis muscle and splenius capitis muscle of a patient with arthritis. The patient can also suffer from headaches, such as chronic or episodic migraines. In some examples, the botulinum toxin administered is from about 5 to about 2500 units of a botulinum toxin type A or from about 100 to about 25,000 units of a botulinum toxin type B. An exemplary administered amount of botulinum neurotoxin can be from about 5 units to about 2500 units, depending upon factors such as the botulinum neurotoxin serotype used, the mass of the patient treated and the severity of the patient's condition, of course.

In one detailed embodiment of a method for treating a respiratory disorder and/or coronary risk factor and/or arthritis in a patient, according to the present invention, intramuscular administration of a therapeutically effective amount of a botulinum toxin type A to each of the frontalis, glabellar, occipitalis, temporalis, masseter, trapezium, semispinalis and splenius capitis muscles of a patient in need thereof, that is, with arthritis, a respiratory disorder and/or coronary risk factor, thereby treating the arthritis and/or respiratory disorder and/or coronary risk factor of the patient.

In still other aspects, the present invention provides for treatment of an arthritis pain in a patient in need thereof comprising the step of intramuscular administration of a therapeutically effective amount of a botulinum toxin type A or a botulinum toxin type B to at least two muscles selected from the group consisting of a frontalis muscle, glabellar muscle, occipitalis muscle, temporalis muscle, masseter muscle, trapezius muscle, semispinalis muscle and splenius capitis muscle of the patient. In particular embodiments, the patient experiences arthritis pain located at joint of an extremity (i.e. an arm of leg), for example, such as a wrist joint, finger joint, elbow joint, toe joint, ankle joint, hip joints and knee joint, shoulder joint. In some embodiments, the botulinum toxin administered is from about 5 to about 2500 units of a botulinum toxin type A or from about 100 to about 25,000 units of a botulinum toxin type B. Additionally, the patient may also suffer a headache, such as a tension headache, a migraine headache, an episodic migraine, a chronic migraine, a cluster headache, a sinus headache, a chronic progressive headache, a hormone headache and a cervogenic headache. In particular instances, the migraine headache can be a chronic migraine or episodic migraine.

DEFINITIONS

The following definitions apply herein.

"About" means plus or minus ten percent of the value so qualified.

"Biocompatible" means that there is an insignificant inflammatory or immunogenic response from use of a botulinum toxin according to the present invention.

"Biologically active compound" means a compound which can effect a beneficial change in the subject to which it is administered. For example, "biologically active compounds" include neurotoxins.

"Therapeutically effective amount" as applied to the biologically active compound (such as a botulinum toxin) means that amount of the compound which is generally sufficient to effect a desired change in a patient. For example, where the desired effect is treatment of a coronary risk factor and/or a respiratory disorder, an effective amount of the compound is that amount which causes an alleviation of the a coronary risk factor and/or a respiratory disorder, as observed clinically, without a significant systemic toxicity resulting.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron.

"Treatment" or "treating" means any treatment of a disease in a mammal, and includes: (i) preventing the disease from occurring or; (ii) inhibiting the disease, i.e., arresting its development; (iii) relieving the disease, i.e., reducing the incidence or severity (i.e. alleviation) of symptoms of or causing regression of the disease, such as, for example, by a reduction in blood pressure, reduction in number and/or severity of asthma attacks, a reduction in a need for, or elimination of, a medication associated with a respiratory disorder or coronary risk factor, reduced blood cholesterol or triglyceride levels, for example. Treating or alleviation of at least one symptom associated with arthritis, a coronary risk factor or respiratory disorder is considered to be treating the particular arthritis, coronary risk factor and/or respiratory disorder suffered by the patient in need of the treatment.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention

DESCRIPTION

The present invention is based upon a method for treating arthritis and/or a coronary risk factor and/or a respiratory disorder by local administration of a botulinum neurotoxin to a head, neck or shoulder location of a patient with a coronary risk factor and/or a respiratory disorder. Thus and in particular, treatment is preferably by intramuscular injection of a botulinum neurotoxin to a head, neck or shoulder location of the patient. Most preferably, botulinum neurotoxin type A is utilized, permitting delivery of long-lasting therapeutic amounts of a bioactive botulinum toxin to treat the arthritis and/or coronary risk factor and/or respiratory disorder. After administration of the botulinum neurotoxin in accordance with the teachings of the present invention, at least one symptom of at least one of a coronary risk factor or symptom of a respiratory disorder and/or arthritis are alleviated.

Administration of a botulinum neurotoxin can be used to treat a coronary risk factor, arthritis pain and respiratory disorders is surprising because of the apparent lack of systemic connection or control/biofeedback mechanisms between the head, neck and/or shoulder location to which the botulinum toxin is administered and the at least one coronary risk factor and/or respiratory disorder and/or arthritis pain to be treated. Additionally, in some instances, patients in need of treatment of their coronary risk factor and/or arthritis pain and/or respiratory disorder(s) can also have a headache, such as a tension headache, a migraine headache, an episodic migraine, a chronic migraine, a cluster headache, a sinus headache, a chronic progressive headache, a hormone headache and a cervogenic headache.

Additionally, whereas the botulinum neurotoxin is to be administered at a head, neck or shoulder location, at least one arthritis symptoms is alleviated at distal joint location(s), such as a finger joint, a toe joint, an ankle joint, an elbow joint, a knee joint, a wrist joint and a hip joint for example.

The therapeutic dose of administered botulinum toxin is such that there are nominal or insignificant systemic effects due to any botulinum neurotoxin which passes into the circulatory system.

Preferably, the botulinum to neurotoxin used to practice a method within the scope of the present invention is one of the serotype A, B, $C_1$, D, E, F or G botulinum neurotoxins. Preferably, the botulinum neurotoxin used is botulinum toxin type A, because of its high potency in humans, ready availability, and known safe and efficacious use for treatment of various disorders for over two decades.

The present invention includes within its scope the use of any botulinum neurotoxin which has a therapeutic effect to treat arthritis or coronary risk factor or respiratory disorder according to the present invention (i.e. administered to a head neck or shoulder location). For example, neurotoxins made by any of the species of the toxin producing *Clostridium* bacteria, such as *Clostridium botulinum, Clostridium butyricum*, and *Clostridium* beratti can be used or adapted for use in the methods of the present invention. Additionally, all of the botulinum serotypes A, B, $C_1$, D, E, F and G can be advantageously used in the practice of the present invention, although type A is the most preferred serotype, as explained above.

The present invention includes within its scope: (a) a botulinum neurotoxin complex as well as a pure botulinum neurotoxin obtained or processed by bacterial culturing, toxin extraction, concentration, preservation, freeze drying and/or reconstitution and; (b) modified or recombinant botulinum neurotoxin, that is botulinum neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of botulinum neurotoxins so made, and includes botulinum neurotoxins with one or more attached targeting moieties for a cell surface receptor present on a cell.

Botulinum toxins for use according to the present invention can be stored in lyophilized or vacuum dried form in containers under vacuum pressure. Prior to lyophilization, the botulinum toxin can be combined with pharmaceutically acceptable excipients, stabilizers and/or carriers, such as albumin. The lyophilized or vacuum dried material can be reconstituted with saline or water in accordance with known methods of reconstitution. Additionally, the botulinum toxin for use in accordance with the method herein disclosed can be provided as ready-to-use injectable solutions from their manufacturer. For example, Myobloc® (Botulinum Toxin Type B) is provided as an injectable solution in vials containing 5000 units of botulinum toxin type B per mL in 0.05% human serum albumin, 0.01 M sodium succinate, 0.1 M sodium chloride at approximately pH 5.6.

Methods for determining the appropriate dosage is generally determined on a case by case basis by the attending physician. Such determinations are routine to one of ordinary skill in the art (see for example, Harrison's Principles of Internal Medicine (1998), edited by Anthony Fauci et al., 14$^{th}$ edition, and published by McGraw Hill). Appropriate dosage administration of botulinum toxin, and modification thereof, is a feature of administration that one of ordinary skill in the art is familiar. Exemplary dosages are provided below to guide the practitioner. However and in accordance with common medical practice, dosages may be increased or decreased, according to the particular outcome/results observed after a particular botulinum neurotoxin is administered to a particular patient at a particular location.

For example, Table 1 provides a medical practitioner with a guide to exemplary amounts of administration (location and units) of a botulinum toxin type A (BOTOX®) to a patient:

TABLE 1

| Muscle Area | Number of Units | Bilateral Injection | Total Dose (U) |
|---|---|---|---|
| Frontalis/Glabellar | About 25 to about 40 | No | About 25 to about 40 |
| Occipitalis | About 10 | Yes | 20 |
| Temporalis | About 10 to about 25 | Yes | About 20 to about 50 |
| Masseter (optional) | About 0 to about 25 | Yes | About 0 to about 50 |
| Trapezius | About 10 to about 30 | Yes | About 20 to about 60 |
| Semispinalis | About 5 to about 10 | Yes | About 10 to about 20 |
| Splenius capitis | About 5 to about 10 | Yes | About 10 to about 20 |
| Total Dose Range | | | About 105 to about 260 |

BOTOX® is available from Allergan, Irvine, Calif., and each vial contains 100 U of *Clostridium botulinum* toxin type A, 0.5 mg albumin (human), and 0.9 mg sodium chloride in a sterile, vacuum-dried form without a preservative. One U corresponds to the calculated median lethal intraperitoneal dose ($LD_{50}$) in mice. The vials are stored in a freezer between −20 degrees Centigrade and −5.degree Centigrade before use. Toxin can be administered to only one of the muscles of Table 1 or at least two or more, as best seen fit by the medical practitioner. Note, as set forth in the table above, as little as 5 units of BOTOX® can be administered if only one muscle is injected with the botulinum toxin. The units listed above are of BOTOX®, but different serotypes or strains of a botulinum toxin can be used, and different amounts may be administered. For example, about 3-4 times of DYSPORT® (a botulinum toxin type A) may be utilized (i.e. up to about 1040 units), and about 40-50 times of NEUROBLOC®/MYOBLOC® may be utilized (i.e. up to about 13,000 units) relative to BOTOX® units, to achieve a desired therapeutic effect, respectively.

EXAMPLES

The following examples set forth specific compositions and methods encompassed by the present invention and are not intended to limit the scope of the present invention.

Example 1

Method for Treating Asthma

A 20 year old male presents with wheezing, shortness of breath and coughing. He states that he coughs and wheezes practically every day for about 6 hours per day, the coughing and wheezing being exacerbated when he exerts himself playing tennis or basketball. On occasion he reports that he sometimes experiences tightness of the chest, which ends his games early. After a review of the patient's symptoms, medical history, and physical examination, his physician conducts a pulmonary (lung) function test, utilizing a spirometer. The physician determines that the patient suffers from asthma, and he is provided with an inhalable short-acting medication, inhaled/metered albuterol (β2-adrenergic receptor agonist), to inhale when his chest tightening and coughing is exacerbated. After 1-month, the patient returns to his physician to report the inhaler is not effective, and that he continually misplaces it, which does not allow him to inhale the albuterol when he needs it most.

The patient is therefore treated by administration of a botulinum neurotoxin into one or more head, neck and shoulder muscles, for example, by intramuscular administration. In particular, a botulinum toxin type A (BOTOX®) is administered in the following pattern and amounts. Intramuscularly and utilizing a 26-gauge needle, about 5 units of botulinum toxin type A is symmetrically and bilaterally injected at two sites, separated by 1 cm, into each of the occipitalis muscles (4 total injections into the occipitalis muscles, for about 20 units), 5 units is symmetrically and bilaterally injected at four sites in the frontalis muscle (2 injection sites at about 0.5 inch above the eyebrows and vertical to the medial canthus, and 2 injection sites, each 1 inch laterally and upward to the hairline in a "V" configuration from the first two injections, for a total of 20 units into the frontalis muscle), and 1 injection of 5 units into approximately the center of each of the temporalis muscles (total of 10 units into the temporalis muscles) for a total of about 50 units of botulinum toxin.

At a follow up one month later, the patient reports that within 7 days of botulinum toxin administration he wheezes less than 1.5 hours/day and that he can participate in and complete a whole game of tennis. An in-office measurement of lung function shows improvement of forced vital capacity (amount of air exhaled with force after inhalation as deeply as possible) as well as forced expiratory volume (amount of air you can exhale with force in one breath, measured at 1 second (FEV1), 2 seconds (FEV2), or 3 seconds (FEV3).

Example 2

Method for Treating Bronchitis

A 39 year old female presents with a rough cough that produces copious amounts of mucus. Additionally, the patient complains of shortness of breath, fatigue, swelling of her feet and ankles and has blue-tinged lips as a result of low levels of oxygen, and is running a low grade fever of about 38.5 degrees Celsius. The patient has had these symptoms for over two months, and after conducting a pulmonary function test (PFT) and high resolution computed tomography (HRCT) to observe her lungs, and her physician notes she has a heavy mucus buildup in her bronchi. The patient is treated with bronchodilator medications and instructed to get at least nine hours of sleep per day. The patent returns after two months, reporting no alleviation of her symptoms. The doctor determines that she is suffering from bronchitis and decides to administer a botulinum toxin to her temporalis, trapezius and frontalis muscles.

Taking an imaginary vertical line down the midline and front of the patient's forehead, the forehead is imagined to be divided into two halves. Three injections of 10 units each of botulinum toxin type A (DYSPORT®) are made laterally and midway between the hairline and eyebrows, to the left from this imaginary midline and towards the patients temple, evenly spaced apart about 1.5 cm. The same is done to the right, for a total of six injections into the frontalis muscle (60 units of DYSPORT® into the forehead). Additionally, one injection of 20 units is administered into each of the two temporalis muscles (40 units total of DYSPORT® to temporalis muscles), and 50 units is administered into each of the trapezius muscles (100 units total of DYSPORT® into the trapezius muscles). Within 3 days, the patient reports that the swelling of her feet and ankles has decreased and she no longer coughs when breathing and no longer has blue-tinged lips. Additionally, the symptoms of her bronchitis remain alleviated for approximately 3 months.

Example 3

Method for Treating COPD

A 57 year old chain-smoking man presets with a hacking, chronic cough. He informs his doctor that he has smoked since he was 10 years old and has several very bad colds each winter for the last few years. He further informs the doctor that he has the most difficulty breathing in the morning and evening. The patient finds that short walks result in breathlessness and walking up the stairs in front of his house is difficult. After a thorough physical exam, the doctor determines that patient has both chronic bronchitis and emphysema (COPD), which are obstructing his airflow (in and out of his lungs), thus interfering with normal breathing.

The patient is treated by administering from about 100 to 200 units of a botulinum toxin type A (BOTOX®) (or from 4000 to about 8000 units of a botulinum toxin type B (MYOBLOC®). Into each of his trapezius muscles, 20 units of botulinum toxin type A is administered (total of 40 units bilaterally) and 10 units is administered to each of the semispinalis dorsi, semispinalis cervicis semispinalis capitis (total of 60 units bilaterally). Within 10 days after this administration protocol, the patient's breathlessness and walking up stairs is alleviated, and coughs only in the early morning.

Example 4

Method for Treating Hypertension and Obesity

A 43 year old partner at a successful advertising agency complains to his doctor that he hears ringing in his ears and is suffering dizzy spells at least once a day. The doctor notes that his 5 foot 6 inch, 302 pound patient appears to sweat continuously and appears to be under a great amount of stress. Taking his blood pressure, it is noted that it reads 202/120 mmHg. Despite previous prescriptions of 2-[4-[2-hydroxy-3-(1-methylethylamino)propoxy]phenyl]ethanamide, a β1 receptor specific antagonist (trade name Tenormin), his patient's hypertension is unaffected. The doctor administers about 10 units of a botulinum toxin type A (BOTOX®) to each of the muscles listed in Table 1 (for a total of about 140 units). During a follow up visit two weeks later, the patient's blood pressure is taken again, this time reading at 155/90 mmHg, a positive alleviation of the hypertension. It is also noted that the patient has lost approximately 6 pounds since his last weigh in. The patient also reports that since administration of the botulinum toxin, he no longer experiences ringing in his ears and has only been dizzy only once since his last visit.

The doctor follows up with the patient a month later, and notes that his blood pressure now reads at 142/87 mmHg and the patient weights 6 pounds less. It is determined that the patient be administered a regime of botulinum toxin, as administered to him in the first instance, every 4.5 months. As a result and within one year, the patient loses 53 pounds and has an average blood pressure of 136/78 mmHg.

Example 5

Method for Treating Diabetes

A 64 year old woman, 5 feet, 2 inches tall and weighing 187 pounds, presents to her doctor, complaining of headaches, blurred vision and an insatiable thirst. Her physician determines her fasting blood glucose level after an overnight fast (not eating anything after midnight). The patient registers a value of 152 mg/dl the first time her blood glucose level is measured, and 163 mg/dl a week later. It is determined, after conducting an oral glucose tolerance test performed in the doctor's office, that the patient is diabetic (oral glucose tolerance tests shows that her blood glucose level at 2 hours is equal to or more than 223 mg/dl).

She is administered 200 units of a botulinum toxin type B (e.g. MYOBLOC®) intramuscularly into each of her temporalis muscles on each side of her head, at points approximately 1 inch from the top of her earlobe and towards the head's apex (two injections for a total of 400 units of a botulinum toxin type B into the temporalis muscles), and 200 units bilaterally and about one inch above the top of her eyebrow arches, into the frontalis (two injections for a total of 400 units of a botulinum toxin type B in the frontalis) and 100 units into each of two injections into glabellar muscle, utilizing her glabellar lines as guides (two injections for a total of 200 units of botulinum toxin type B), for a grand total of 1000 units of botulinum toxin type B. Within eight days, the patient reports that her thirst has lessened and no longer experiences headaches. At the doctor's office 2 months later, an oral glucose tolerance test reveals that the patient has impaired glucose tolerance (i.e., a 2-hour glucose result from an oral glucose tolerance test registering 145 mg/dl) instead of diabetes, which is lower that when first measured (223 mg/dl).

Example 5

Method for Treating Hyperlipidemia

A 26 year old male presents with a total blood cholesterol level of 370 mg/dL, an LDL cholesterol level of 210 mg/dL and an HDL level of 32 mg/dL. Although the patient exercises regularly (3×/week for 1 hour each time) and takes a statin prescribed by his doctor to lower his LDL levels, his lipid profile does not improve. H is physician decides that the patient will be administered a botulinum toxin type A (BOTOX®), where about 20 units evenly divide among 4 injection points are intramuscularly administered into his glabellar lines, and about 50 units into each of his temporalis muscles (for a total of 100 units into the temporalis muscles), and about 50 units into each of his trapezius muscles (about 100 units into the trapezius muscles), for a total administration of about 220 units of botulinum toxin type A.

After 1 month, the patient returns and his cholesterol levels are lower, now having a total blood cholesterol level of 260 mg/dL and his LDL cholesterol level is 162 mg/dL and HDL level is 40 mg/dL. After one year, the doctor notes that the patient's total blood cholesterol level is now 210 mg/dL and his LDL cholesterol level is 110 mg/dL and has an HDL level of 42 mg/dL.

Example 6

Method for Treating Arthritis

A 57 year old mechanic reports to his doctor that pain due to the arthritis in his hands and fingers is becoming unbearable, and rates his pain at a 9 on the visual analogue scale for pain (VAS) at the doctor's office. Application of various topical creams that contain ingredients such as methyl salicylate, menthol and capsaicin are simply ineffective. The physician decides to administer a botulinum toxin type A in order to treat the arthritis to the patient's trapezius, frontalis and occipitalis muscles.

The doctor administers a total of 100 units of a botulinum toxin type A (BOTOX®) as follows: about 50 units into the frontalis muscle (five injections of about 10 units each across the forehead of the patient (along an approximately horizontal midline between the eyebrows and hairline of the patient) and 40 units into the trapezius muscles (two injections/10 units each into the left and two injections/10 units each into the right trapezius, for a total of 40 units into the trapezius muscles) and 10 units into the occipitalis muscles (two injections/5 units each). After about 8 days, the patient reports that his arthritic pain is alleviated and ranks his pain at only a 2 on the same VAS. The arthritic pain remains alleviated for about at least about 3 months.

Example 7

Method for Treating Arthritis

A 39 year old female long distance runner (and known osteoarthritis sufferer) complains to her family doctor that her knee joints ache most of the time, and that her running regimen is being hampered by the pain, rating as an 8 on the doctor's visual analogue scale for pain (VAS). After prescribing NSAIDs for 2 months, the patient reports that no improvement or alleviation of the pain. Accordingly, the doctor decides to treat the arthritis pain by administration of a botulinum toxin into the splenius capitis and temporalis muscles. About 50 units of a botulinum toxin type A (DYSPORT®) is bilaterally injected, i.e. about 25 units into the left and right splenius capitis muscles, and 100 units is bilaterally injected, i.e. 50 units into each of her temporalis muscles.

After 10 days, the patient reports returns to the doctor's office for a follow up and reports that the pain in her knees is alleviated, and now when asked to rate her pain on the visual analogue scale for pain (VAS), she rates it as a 3, a good and desirable improvement. The patient is similarly administered the botulinum toxin every 6 months thereafter.

Compositions and methods according to the invention disclosed herein have many advantages, including that a botulinum toxin can be used to provide therapeutically effective treatment of coronary risk factors, a respiratory disorder and arthritis.

All references, articles, publications and patents and patent applications cited herein are incorporated by reference in their entireties.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes formulations wherein two or more neurotoxins, such as two or more botulinum toxins, are administered concurrently or consecutively. For example, botulinum toxin type A can be administered until a loss of clinical response or neutralizing antibodies develop, followed by administration of a botulinum toxin type B or E. Alternately, a combination of any two or more of the botulinum serotypes A-G can be locally administered to control the onset and duration of the desired therapeutic result.

Furthermore, non-neurotoxin compounds can be administered prior to, concurrently with or subsequent to administration of the neurotoxin formulation so as to provide an adjunct effect such as enhanced or a more rapid onset of denervation before the neurotoxin, such as a botulinum toxin, begins to exert its therapeutic effect.

The present invention also includes within its scope the use of a neurotoxin, such as a botulinum toxin, in the preparation of a medicament for use to treat a treating coronary risk factor and/or respiratory disorders and/or arthritis by administration of the botulinum toxin to a head, neck and/or shoulder location of a patient with a coronary risk factor and/or respiratory disorder and/or arthritis.

Accordingly, the spirit and scope of the following claims should not be limited to the descriptions of the preferred embodiments set forth above.

What is claimed is:

1. A method for treating osteoarthritis pain in a patient in need thereof, the method comprising the step of intramuscular administration of a therapeutically effective amount of botulinum toxin bilaterally to the splenius capitis and temporalis muscles of a patient suffering osteoarthritis pain, thereby decreasing the osteroarthritis pain.

2. The method of claim 1 wherein the botulinum neurotoxin is botulinum neurotoxin type A.

3. The method of claim 1, wherein the osteoarthritis pain experienced by the patient is experienced in a knee joint.

4. The method of claim 1, wherein the patient has no improvement with an oral medication.

5. The method of claim 4, wherein the oral medication is a non steroidal anti-inflammatory drug, COX-2 inhibitor, analgesics or a corticosteroid.

6. The method of claim 1, wherein the botulinum toxin administered is from about 5 units to about 2500 units of a botulinum toxin type A or from about 100 to about 25,000 units of a botulinum toxin type B.

* * * * *